(12) United States Patent
Felix-Faure

(10) Patent No.: US 7,776,012 B2
(45) Date of Patent: Aug. 17, 2010

(54) PREFILLED SYRINGE WITH MEANS OF DETECTING THE DISPLACEMENT OF THE PISTON

(75) Inventor: Catherine Felix-Faure, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 639 days.

(21) Appl. No.: 10/556,619

(22) PCT Filed: May 25, 2004

(86) PCT No.: PCT/FR2004/001295

§ 371 (c)(1),
(2), (4) Date: Mar. 12, 2007

(87) PCT Pub. No.: WO2004/105843

PCT Pub. Date: Sep. 12, 2004

(65) Prior Publication Data

US 2007/0265567 A1 Nov. 15, 2007

(30) Foreign Application Priority Data

May 26, 2003 (FR) .................................. 03 06340

(51) Int. Cl.
*A61M 5/00* (2006.01)
*A61M 5/315* (2006.01)
(52) U.S. Cl. ....................................... 604/111; 604/218
(58) Field of Classification Search ................. 604/111, 604/181, 187, 221, 110, 218
See application file for complete search history.

(56) References Cited

U.S. PATENT DOCUMENTS

| 3,366,113 | A | * | 1/1968 | Hobbs | 604/111 |
| 4,480,760 | A | * | 11/1984 | Schonberger | 215/230 |
| 4,890,627 | A | * | 1/1990 | Haber et al. | 600/578 |
| 4,890,763 | A | * | 1/1990 | Curiel | 229/102 |
| 5,242,405 | A | * | 9/1993 | Howe | 604/125 |

FOREIGN PATENT DOCUMENTS

DE 199 25 621 A1 * 12/1999

* cited by examiner

*Primary Examiner*—Matthew F Desanto
(74) *Attorney, Agent, or Firm*—David M. Fortunato; Cohen Pontani Lieberman & Pavane LLP

(57) ABSTRACT

A device (1) for medical use, of the prefilled ready-to-use syringe type, comprising a tubular body (2) comprising, at its distal end (4), a tip (5) to take a needle and, at its proximal end (12), a piston (3) able to slide inside the said tubular body (2), the said piston (3) being arranged in an initial position, with respect to the tubular body (2), defining an internal working volume (8) at least partially filled with a medicinal liquid (9), the piston (3) being connected to a rod (11) for actuating the said piston, characterized in that the tubular body (2) is provided, on its internal face (13), with a means (14) of detecting the movement of the piston (3), the said means (14) being situated between the initial position of the piston and the proximal end (12) of the tubular body (2).

The present invention also relates to a method for manufacturing such a device.

20 Claims, 1 Drawing Sheet

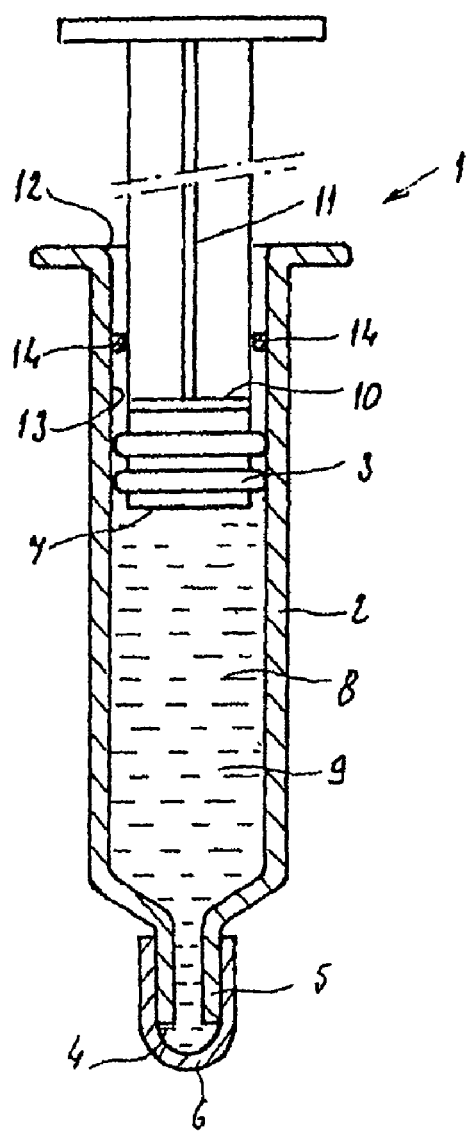
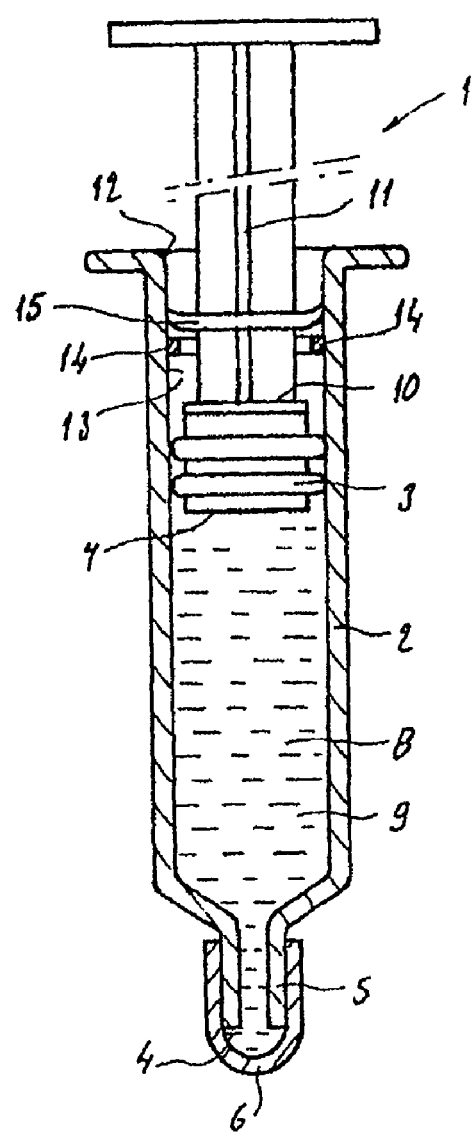

PREFILLED SYRINGE WITH MEANS OF DETECTING THE DISPLACEMENT OF THE PISTON

PRIORITY CLAIM

This is a U.S. national stage of application No. PCT/FR04/01295, filed on May 25, 2004, priority is claimed on that application and on the following application Country: France, Application No.: 03/06340, Filed: May 26, 2003, the entirety of both applications are incorporated herein by reference.

In the field of prefilled ready-to-use syringes, devices have already been described that make it possible to determine whether or not the syringe has already been used. These devices generally relate to the distal end of the syringe, that is to say to the end of the syringe situated near the needle. It has been proposed that the needle be covered by a cap that has to be broken before the syringe can be used.

However, in the case of prefilled syringes, it may also be useful to provide a device making it possible to determine whether the piston of the syringe has been moved, or even removed and then reinstated, so as to determine whether the medicinal liquid present inside the body of the syringe could have been contaminated or even substituted.

During the process of manufacture of this type of syringe, the syringes are filled in a sterile environment and then packaged and possibly sterilized. It is between these two steps, filling and packaging, that the internal chamber of such syringes must not be exposed or that the drug it contains must not be contaminated or substituted.

U.S. Pat. No. 3,126,004 describes a syringe comprising a piston of which the proximal face, coupled to the rod, is covered in wax, this wax extending as far as the interior wall of the syringe. In that document, the movement of the piston breaks the wax and the user thus knows that the syringe has already been used. However, such a device has the disadvantage that when the authorized user wishes to use the syringe, he has to break the wax which breaks up into small pieces likely to contaminate the surroundings in which the medicinal procedure is being performed.

The present invention is aimed at overcoming this problem by providing a prefilled syringe equipped with means for making it possible to determine whether the piston of this syringe could have already been moved, or even withdrawn then reinstated, the said means presenting no risk of contamination when used by an authorized user.

The present invention relates to a device for medical use, of the prefilled ready-to-use syringe type, comprising a tubular body comprising, at its distal end, a tip to take a needle and, at its proximal end, a piston able to slide inside the said tubular body, the said piston being arranged in an initial position, with respect to the tubular body, defining an internal working volume at least partially filled with a medicinal liquid, the piston being connected to a rod for actuating the said piston, characterized in that the tubular body is provided, on its internal face, with a means of detecting the movement of the piston, the said means being situated between the initial position of the piston and the proximal end of the tubular body.

The means of detecting the movement of the piston is situated between the initial position of the piston, that is to say its position after the device has been filled, and the proximal end of the tubular body. The means of detecting the movement of the piston is thus separate from the piston. Because of its position on the tubular body, this position being separate from the initial position of the piston, the means of detecting the movement of the piston according to the invention presents no risk of contaminating the medical environment when the syringe is used by the authorized user. It is by stressing the means of detecting the movement of the piston, as the piston slides, for example to withdraw it from the tubular body or to use the syringe, that the piston stresses the means of detecting the movement of the piston, for example by passing over it.

The device according to the invention makes it possible easily to determine whether the piston has been withdrawn then reinstated. Indeed, the authorized user is informed of the initial configuration of the means of detecting the movement of the piston. Thus, when he is ready to use the syringe, there are two situations that offer themselves to him.

In a first scenario, the means of detecting the movement of the piston has not been stressed and is in its initial configuration or form, in which case the piston has not been moved after filling of the syringe and the user can give the injection simply by pushing the piston towards the distal end of the tubular body. The means of detecting or indicator of movement of the piston being situated above the initial position of the piston, it does not carry a risk of contaminating the medicinal liquid contained in the tubular body.

In the second scenario, where the piston has been removed then reinstated, the means of detecting the movement of the piston has been stressed: the consequence may be that this means has disappeared or that it has changed in appearance, this being so in a way visible or perceivable to the user. In this case, the authorized user knows that he must not use the syringe, there being no certainty over the true nature of the medicinal liquid contained in the tubular body, it being possible, for example, for this liquid to have been substituted by another liquid or contaminated fraudulently with toxic or dangerous elements or through the introduction of another piston.

In this application, the distal end of a part is to be understood as meaning the end furthest from the user of the device and the proximal end is to be understood as meaning the end closest to the user of the device.

In a preferred embodiment of the invention, the tubular body is made of a material that is opaque but translucent. In an even more preferred embodiment of the invention, the tubular body is made of a material that is transparent. In this application, a material that is transparent is to be understood as meaning material that allows objects to be distinguished through its thickness. As a preference, the material of which the tubular body is made is glass or plastic.

In one embodiment of the invention, the means of detecting movement of the piston is in the form of an at least partial coating of the internal face of the tubular body with a material that can be altered by shear or friction. Thus, in one embodiment of the invention, the coating has an initial shape, that is to say the shape after filling and before shearing, different from the one it has in the sheared state. In the present invention, shear in particular is brought about by the passage of the piston over the means of detecting the movement of the piston. As a preference, this material is a thixotropic material. The material of which the coating is made is then in a solid or semisolid state at rest and changes into a liquid state after shear has been applied. For example, this material comprises solid or semisolid microcapsules filled with a liquid substance. These microcapsules burst under shear as the piston passes and release their liquid contents.

In another embodiment, the material is in the viscous state at rest and is dragged along the internal face of the tubular body by the shear effect caused by the passage of the piston. As a preference, this material comprises an ink or an oil, particularly silicon, or a gel. In such a case, depending on the initial amount of material present, traces of material appear on the internal face of the tubular body or, on the other hand, the coating may be completely removed. The appearance of traces or the complete disappearance of the coating are indicators of the prior use of the device and therefore the fact that it has been tampered with.

In a preferred embodiment of the invention, this coating is in the form of a continuous annular wad consisting of a material that can be altered by shear.

In one embodiment of the invention, the annular wad is continuous. For example, the coating may comprise drops of material deposited on the internal face of the tubular body in a radial plane.

In a preferred embodiment of the invention, the means of detecting movement of the piston has, before shear, that is to say in its unstressed form, a different color to the one it has after shear, that is to say in its stressed form. Thus, in the embodiment where the coating comprises microcapsules, the latter may contain a liquid of a different color to that of the exterior casing of the microcapsules. The appearance of the color corresponding to that of the liquid content of the microcapsules directly informs the user that the piston has been moved.

In one embodiment of the invention, the actuating rod is fitted with a flexible flange, fixed to the said rod, making contact with the internal face of the tubular body and situated between the means of detecting the movement of the piston and the proximal end of the tubular body. By virtue of this flange, it is possible to determine whether the piston has been moved towards the distal end of the tubular body. What happens is that the passage of the flange over the means of detecting the movement of the piston stresses this means which changes appearance or disappears as explained above in respect of the piston. Thus, by virtue of this flange, any movement of the piston, whether this be towards the distal end or, on the other hand, towards the proximal end of the tubular body, can be detected by the authorized user.

The invention also relates to a method of manufacturing a device for medical use, of the prefilled ready-to-use syringe type, comprising a tubular body comprising, at its distal end, a tip to take a needle, a piston able to slide inside the tubular body and a means of detecting the movement of the piston, comprising the following successive steps:
1. The distal end of the tubular body is closed,
2. The tubular body is filled with a medicinal liquid up to a given height in the tubular body,
3. The piston is fitted in such a way as to enclose the medicinal liquid in the tubular body without air, and
4. The part of the internal face of the tubular body that is situated between the piston and the proximal end of the tubular body is at least partially coated.

As a preference, after step 4, an actuating rod is fitted to the piston, fixing it in place by screwing or snap fastening. As a preference, this actuator rod is equipped with a flexible flange making contact with the internal face of the tubular body and situated between the coating and the proximal end of the tubular body.

Advantageously, the coating is performed using a brush, a nozzle or a pad.

The invention will be better understood from the description that follows, with reference to the attached drawing:

FIG. 1 is a view in section of a device according to the invention, after filling, FIG. 2 is a view in section of an alternative form of the device according to the invention, after filling.

FIG. 1 depicts a device 1 comprising a tubular body 2 made of glass and a piston 3 able to slide inside the tubular body. At its distal end 4 the tubular body 2 has a tip 5 to take a hollow needle (not depicted), this tip being closed by a plug 6.

The lower end 7 of the piston defines, in its initial position, that is to say after filling, inside the tubular body 2, an internal working volume 8 filled with a medicinal liquid 9. The upper end 10 of the piston 3 is connected to an actuating rod 11 protruding from the proximal end 12 of the tubular body 2.

The tubular body 2 is provided, on its internal face 13, with a continuous annular wad 14, attached by coating, incorporating a colored ink and situated between the position of the piston 3 that is shown in FIG. 1, that is to say the position after filling, and the proximal end 12 of the tubular body 2.

Thus, if someone withdraws or extracts the piston 3 from the tubular body 2 towards its proximal end, after the step of filling the said body, but before the device is packaged, and soils the medicinal liquid or substitutes another liquid of different nature or quality for this liquid, the ink incorporated into the annular wad will be rubbed off or spread in traces over the internal face 13 of the tubular body 2 as the piston passes towards the outside. The absence of ink or the presence of traces or of runs for example will be immediately visible because of the transparency of the wall of the tubular body 2. In this way, even if the piston is then reinstated in a position identical to its initial position within the tubular body 2, it is possible to determine that it has been withdrawn and then reinstated.

FIG. 2 depicts a device 1 similar to that of FIG. 1 for which the actuating rod 11 is equipped with a flexible flange 15 fixed to the rod 11, making contact with the internal face 13 of the tubular body. The references indicating the same elements as in FIG. 1 have been repeated in FIG. 2. The flange 15 is situated above the annular wad 14. Thus if the piston 3 is pushed towards the distal end 4 of the tubular body 2, this flange passes over the annular wad 14 and stresses it, erasing or spreading the ink in traces over the internal face 13, as before but on the other side of the wad 14, thus indicating to the authorized user that the piston 3 has been moved towards the distal end 4 of the tubular body 2.

With reference to FIGS. 1 and 2, to produce a device 1 according to the invention, use is made of a tubular body 2 comprising, at its distal end 4, a tip 5 to take a needle, for example a hollow hypodermic needle. This distal end 4 is closed with a plug 6. The tubular body 2 is then filled, for example with a medicinal liquid to a determined height in the tubular body 2, this height being defined for example by a dose of medicinal liquid to be injected. The piston 3 is then fitted to enclose the medicinal liquid in the tubular body 2 without air. The part of the internal face of the tubular body 2 situated between the piston 3 and the proximal end 12 of the tubular body 2 is then at least partially coated. An actuating rod 11 can then be added, which rod is fixed to the piston 3 by screwing or snap fastening. Beforehand, a flexible flange 15 may have been fixed to this actuating rod 11 in such a way that the said flange lies between the coating and the proximal end 12 of the tubular body 2, once the actuating rod has been fixed to the piston.

The present invention is not restricted to the embodiments described by way of example in this application.

Appendix A

Abstract:

The present invention relates to an instrument and more precisely to an injection needle which is intended for introducing liquid substances into the tissues. This injection needle comprises a cylinder in which a piston is guided so as to be capable of displacement, wherein said piston is sealed by a piston seal relative to the inner wall of the cylinder. The piston together with the cylinder closing surface, which comprises cannula member, define a cylindrical inner space that can be filled with a liquid substance. The piston seal (19) is covered in a sterile manner by a second seal (11, 18) which is used as a tamper-evident element relative the outer space located outside the cylindrical inner space. The second seal (11, 18) is designed to resist the piston (5) displacement induced by an actuation member (7, 14) until said second seal (11, 18) is broken, removed and/or displaced away from its initial position.

In FIG. 1 is shown an instrument a according to invention for the injection of a medicine 1 in fabrics, which a cylinder 2, which exhibits is manufactured in this case from glass or transparent plastic. As an injection syringe tapers itself the cylinder 2 at an end to a Kanülenansatz 3, on which a not represented Kanüle is put onable. The cylinder shown 2 serves 1 as container and/or as packing of the medicine and is locked from there with a catch 4, which is put on for the catch of the outlet on the Kanülenansatz 3.

In the cylinder 2 a piston 5 in the form of a rubber or a Plastikpfropfes is stored relocatable, its extent over a piston seal against the inner wall 6 of the cylinder 2 is sealed. The cover surface of the piston 5 and the cover surface of the cylinder 3 exhibiting turned to the interior the Kanülenansatz 3 limit the cylinder interior in that the medicine 1 are. Around the sterility of the medicine 1 in the interior to ensure the piston seal is sterilely taken off as entrance from the environment to the interior by a second poetry 18.

In the remark example after FIG. 1 is the second poetry 18 a foil made of plastic or metal, which depresses for a stamp 7 (FIG. 2) intended depressing opening B of the cylinder 2 completely locks. The foil poetry 18 is leavable (arrow A) held by the grasps 9 of the cylinder 2 basic extent range of the depressing opening 8 by sticking, by Ansiegeln or by welding. Before putting a stamp 7 in the foil poetry 18 serving as originality protection must be completely taken off. Thus the poetry 18 opposes the admission of the piston 5 by the actuator (stamp) 7 so for a long time, until this is distant. It is also conceivable the fact that the second poetry is a cover, which locks the depressing opening as originality catch, until it removed and so that from its original situation is moved.

The execution form after FIG. 2 likewise 1. serves around the originality of contents to ensure is on the one hand the catch 4 over a protection 10 put on on the Kanülenansatz 3 with the ground of the cylinder 2 connected as packing for the medicine. The protection 10 is formed in this case of a leaving foil, which surrounds the Kanülenansatz 3 approximately. Before the use the catch 4 is removed (FIG. 4b) whereby the foil 10 tears off and partly at the catch and partly at the ground of the cylinder remains.

The passage of the cylinder 2 is again locked by a piston 5, whereby this by a leaving foil 11 diendende as the second poetry with the inner wall 6 of the cylinder 2 is connected. The leaving foil 11 is in such a manner welded at the cover surface of the piston 5 arranged to the outside space that the piston seal 19 is completely covered. With the use, i.e. with shifting or rotating the piston 5 in the cylinder, the leaving foil 11 is destroyed and remains in remainders of 12 at the inner wall 6 of the cylinder and at the piston 5. as in the example after FIG. 1 can be the leaving foil 11 also welded at the edge of the depressing opening or moulded on. With a soundness of the leaving foil 11 contents of the cylinder are thus hermetically enclosed.

In this execution form the operating organ designed as stamp 7 is solvable fastenable at the cover surface of the piston 5. In addition the cover surface points a mounting plate element 13a (FIG. 2a) on into the one appropriate at the stamp 7 attached and a key of screen end counterpart 13bis appli-cable. With in such a way formed catch it can concern around a screwing or a plug connector or a bayonet fixing. Such put-compatible stamps 7 is to be used for several devices. It can be changed depending upon need.

The execution forms after the FIGS. 3 and 4 exhibits at the piston 5 stationarily attached stamps 14. With the injection syringe after Fig. it concerns 3 a Einmalspritze, whose piston 5 is pushed in almost up to the ground of the cylinder 2 and whose cylinder inner wall 15 by a leaving foil 16 the used with the outside space in connection is locked. The leaving foil 16 is on the one hand at the neck of the stamp close of the pressure plate 17 and on the other hand welded or angeformt at the cylinder inner wall 15 thereby. The Kanülenansatz 3 can be locked optionally by a well-known catch. When drawing the syringe up tears the leaving foil 16, which protected the inner wall 15 up to this time a contamination.

In the Fig. a syringe serving as container is represented 4, in whose interior a medicine 17 is. The catch of the Kanülenansatz 3 is already decreasing, so that the syringe is ready for use after the plug-on of a Kanüle. To the protection the leaving foil 20 taking the piston seal off again on the one hand 14 and on the other hand at the inner wall 15 of the cylinder is attached at the stamp. The leaving foil 20 tears up when pushing the piston 5. in.

The invention claimed is:

1. A device for medical use, of the prefilled ready-to-use syringe type, comprising:
a tubular body comprising, at its distal end, a tip configured to receive a needle and, at its proximal end, a piston configured to slide inside the said tubular body, the piston being arranged in an initial position with respect to the tubular body and defining an internal working volume at least partially filled with a medicinal liquid, the piston being connected to a rod for actuating the piston, wherein
the tubular body is provided, on its internal face, with a means of detecting the movement of the piston, the means being situated between and spaced apart from both the initial position of the piston and the proximal end of the tubular body and being separate from the piston, and being in the form of at least a partial coating of the internal face of the tubular body with a material that can be altered by at least one of shear and friction.

2. The device according to claim 1, wherein the material is a thixotropic material.

3. The device according to claim 2, wherein the detection means prior to shearing has a different color than the color it has after shearing.

4. The device according to claim 1 wherein the material comprises an ink, or an oil.

5. The device according to claim 4, wherein the material comprises a silicon, or a gel.

6. The device according to claim 1, wherein the material comprises solid or semisolid microcapsules filled with a liquid substance.

7. The device according to claim 1, wherein the coating is in the form of a continuous annular wad.

8. The device according to claim 1, wherein the coating comprises drops of material deposited on the internal face of the tubular body in a radial plane.

9. The device according to claim 1, wherein the tubular body is made of a material that is opaque but translucent.

10. The device according to claim 1, wherein the tubular body is made of a material that is transparent.

11. The device according to claim 1, wherein the actuating rod is fitted with a flexible flange, fixed to the rod, making contact with the internal face of the tubular body and situated between the means of detecting the movement of the piston and the proximal end of the tubular body.

12. The device according to claim 1, wherein the coating has an initial shape before shearing that is different from a sheared state shape.

13. The device according to claim 1, wherein the coating comprises solid or semisolid microcapsules filled with a liquid substance.

14. A method of manufacturing a device for medical use, of the prefilled ready-to-use syringe type, comprising a tubular body having, at its distal end, a tip configured to take a needle, a piston able to slide inside the tubular body and a means of detecting the movement of the piston, the method comprising:
   closing the distal end of the tubular body;
   filling the tubular body with a medicinal liquid up to a given height in the tubular body;
   fitting the piston to enclose the medicinal liquid in the tubular body without air;
   coating at least a portion of the internal face of the tubular body situated between and spaced a distance from both the piston and the proximal end of the tubular body with a coating configured to provide a visual cue in response to a movement of the piston.

15. The method according to claim 14, further comprising:
   fitting an actuating rod to the piston; and
   fixing the actuating rod in place by at least one of screwing or snap fastening.

16. The method according to claim 15, wherein the actuating rod is equipped with a flexible flange making contact with the internal face of the tubular body and situated between the coating and the proximal end of the tubular body.

17. The method according to claim 14, wherein the coating is performed using at least one of a brush, a nozzle or a pad.

18. A device for medical use, of the prefilled ready-to-use syringe type, comprising:
   a tubular body comprising:
      a tip at its distal end configured to receive a needle;
      at is proximal end a piston configured to slide inside the tubular body, the piston being arranged in an initial position with respect to the tubular body and defining an internal working volume for receiving a medicinal liquid; and
   a rod connected to the piston for actuating the piston; and
   a coating on at least a portion of an internal face of the tubular body situated between and spaced a distance from both the initial position of the piston and the proximal end of the tubular body, the coating being positioned for contact with one of the piston and a flange moveable with the piston when the piston is moved in a direction from its initial position toward the proximal end of the tubular body, the coating configured to be altered by at least one of shear and friction through such contact.

19. The device according to claim 18, wherein the coating is a thixotropic material.

20. A method of manufacturing a device for medical use, of the prefilled ready-to-use syringe type, comprising a tubular body having a proximal end, a tip at a distal end of the tubular body configured to receive a needle, a piston configured to slide inside the tubular body from an initial position at the proximal end toward the distal end, and a coating configured to provide a visual cue in response to a movement of the piston from the initial position toward the proximal end, the method comprising:
   closing the distal end of the tubular body;
   filling the tubular body with a liquid to a given height in the tubular body;
   fitting the piston to enclose the medicinal liquid in the tubular body without air; and
   coating at least a portion of the internal face of the tubular body situated between and spaced a distance from both the piston and the proximal end of the tubular body with a coating, the coating being positioned for contact with one of the piston and a flange moveable with the piston when the piston is moved in a direction from its initial position toward the proximal end, the coating configured to provide a visual cue in response to movement of the piston.

\* \* \* \* \*